United States Patent [19]

Brenner et al.

[11] 3,980,646

[45] Sept. 14, 1976

[54] 3-METHYLPYRAZOLE-5-CARBOXYLATES AND MEDICAMENTS CONTAINING THESE COMPOUNDS

[75] Inventors: Günter Brenner, Tannenweg; Karl Credner, Dusseldorf; Joachim Göring; Manfred Tauscher, both of Gronau, Leine, all of Germany

[73] Assignee: Johann A. Wulfing, Dusseldorf and Neuss, Germany

[22] Filed: Aug. 1, 1975

[21] Appl. No.: 601,316

[30] Foreign Application Priority Data
Aug. 14, 1974   Germany............................ 2439137

[52] U.S. Cl............................ 260/247.2 A; 260/253; 260/311; 424/248; 424/253
[51] Int. Cl.².............. C07D 473/06; A61K 31/535; A61K 31/52
[58] Field of Search...................... 260/247.2 A, 253; 424/248, 253

[56] References Cited

UNITED STATES PATENTS

| 2,924,598 | 2/1960 | Bestian | 260/253 |
| 3,728,346 | 4/1973 | Klingler | 260/253 |
| 3,896,119 | 7/1975 | Klingler | 260/247.2 A |

FOREIGN PATENTS OR APPLICATIONS

| 1,089,763 | 9/1960 | Germany | 260/253 |
| 1,102,750 | 3/1961 | Germany | 260/253 |

*Primary Examiner*—Donald B. Moyer
*Attorney, Agent, or Firm*—Kenyon & Kenyon

[57] ABSTRACT

This invention relates to 3-methylpyrazole-5-carboxylates, to processes for the preparation of said compounds and to pharmaceutical compositions containing said compounds.

3 Claims, 4 Drawing Figures

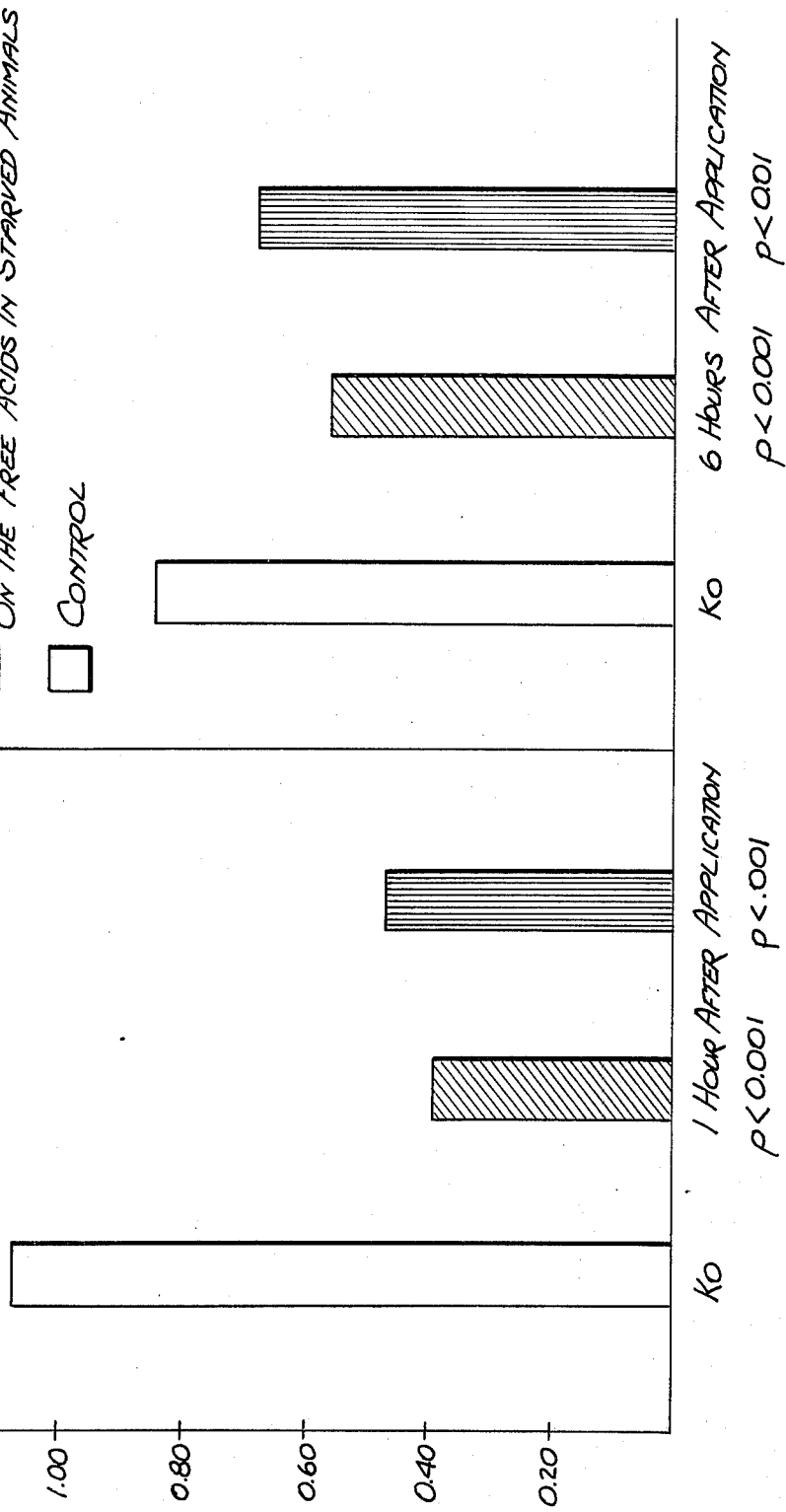

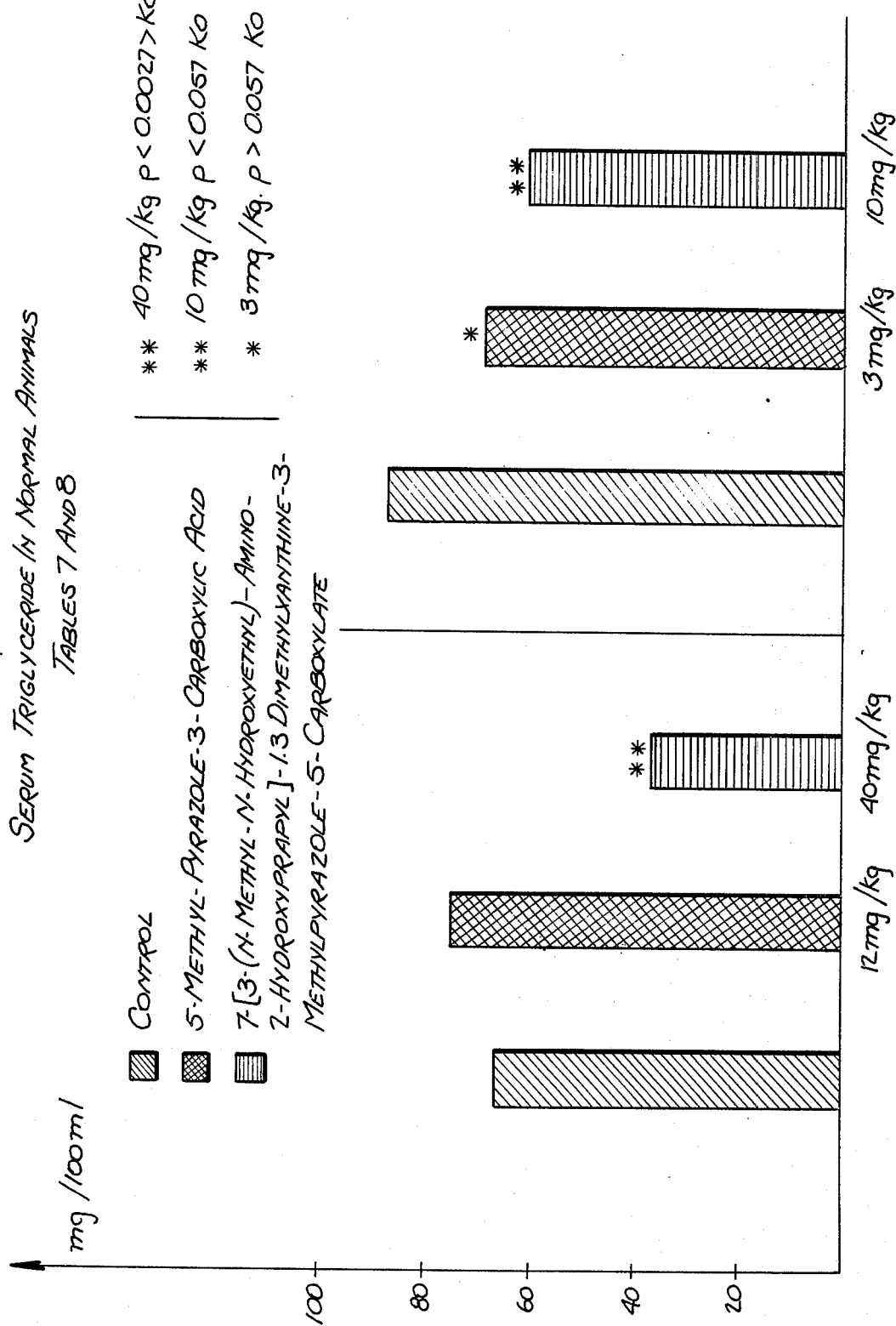

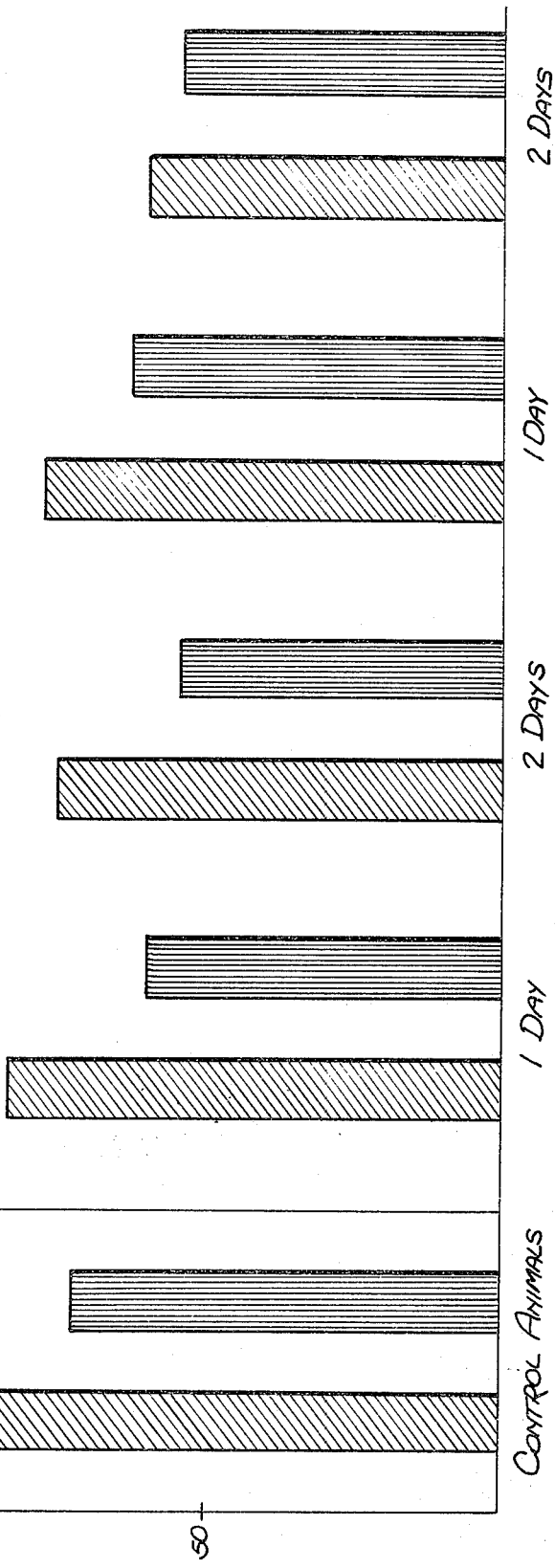

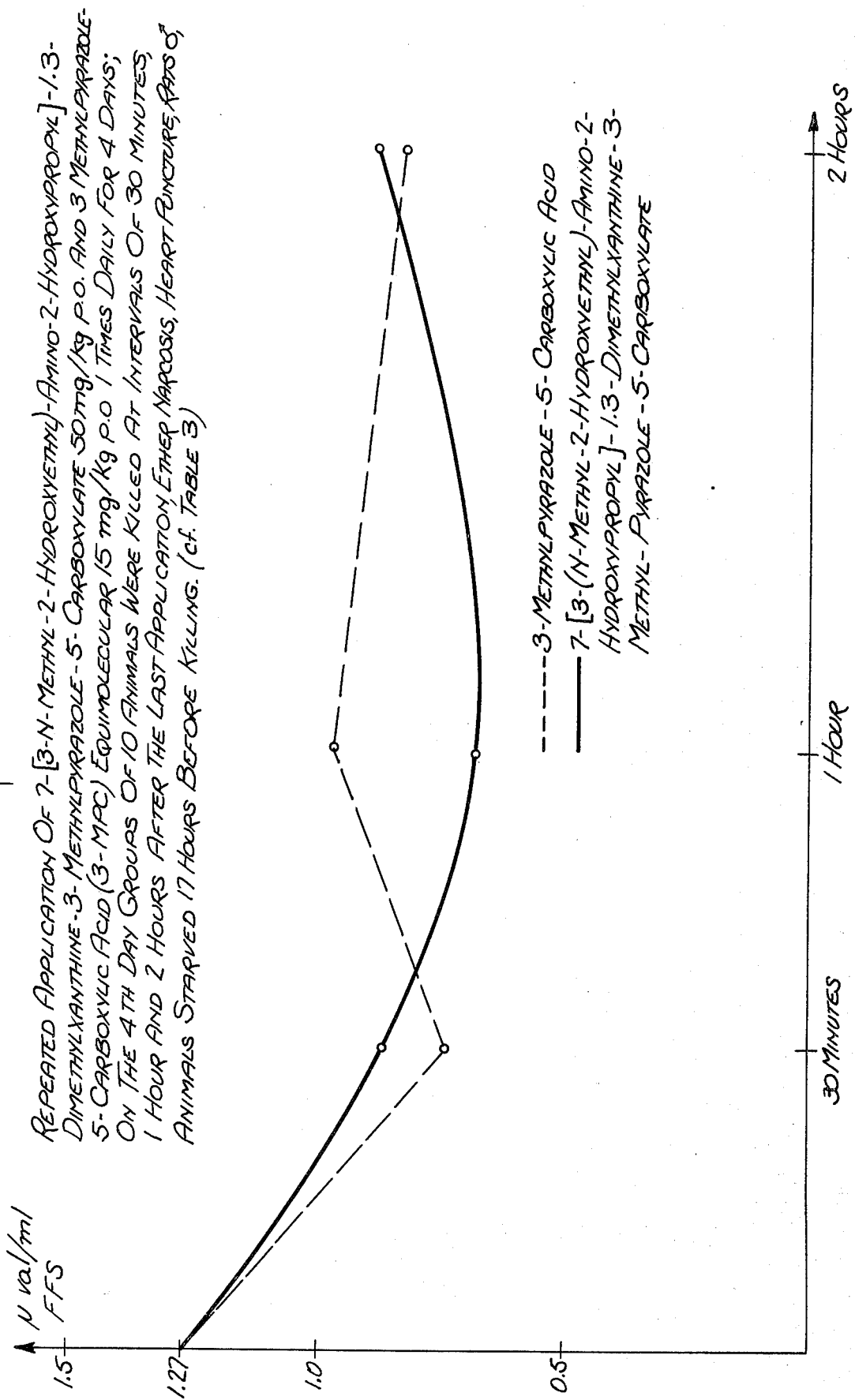

3-METHYLPYRAZOLE-5-CARBOXYLATES AND MEDICAMENTS CONTAINING THESE COMPOUNDS

This invention relates to 3-methylpyrazole-5-carboxylates corresponding to the general formula:

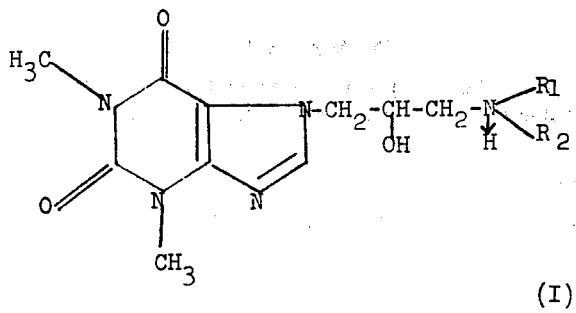

(I)

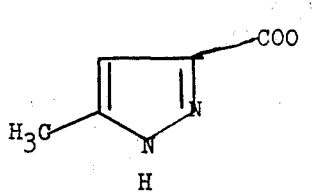

in which $R_1$ and $R_2$ each represent hydrogen, straight-chain or branched alkyl radicals with 1 to 4 carbon atoms, hydroxyalkyl, alkoxyalkyl, aralkyl or norbornyl groups or, together with the nitrogen atom to which they are attached, represent a morpholine radical.

The compounds according to the invention are obtained by reacting correspondingly substituted 1,3-dimethylxanthines corresponding to the general formula:

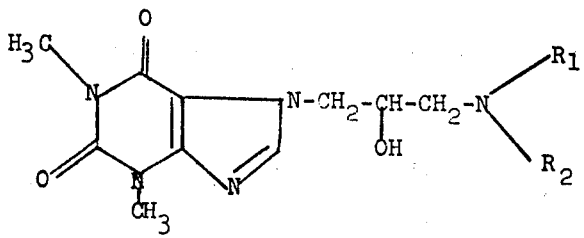

(II)

in which $R_1$ and $R_2$ are as defined above, with 3-methylpyrazole-5-carboxylic acid, preferably in equimolar quantities, in the presence of a solvent.

The reaction is best carried out at a temperature in the range from 40° to 100°C, preferably at the boiling temperature of the solvent.

Suitable solvents are, primarily, lower alcohols such as methanol, ethanol, isopropanol and the various butanols, to which other solvents, such as ethyl acetate, water, etc. may optionally be added in small quantities in order to improve the crystallisability of the claimed compounds.

The theophylline bases of general formula II used for preparation of the compounds of general formula I are employed in pure form or, if purification is not possible, in the form of crude products.

The resulting compounds of formula I are preferably recrystallised from lower alcohols, for example methanol, ethanol, propanol, isopropanol and the various butanols, optionally by the addition of other solvents, such as water, ethyl acetate, acetone, dioxan, or alternatively mixtures of different solvents are used.

The compounds produced in accordance with the invention are distinguished by their pronounced lipolysis-inhibiting activity, their effectiveness in reducing triglyceride and cholesterol level and their low toxicity. 7-[3-(N-methyl-N-2-hydroxyethyl)-amino-2-hydroxypropyl]-1,3-dimethylxanthine-3-methylpyrazole-5-carboxylate has a particularly marked effect.

Hyperlipidaemiae are a serious health risk because they promote the development of arteriosclerosis to a considerable extent. Accordingly, preparations which reduce lipid level, i.e. which reduce the content of triglycerides, free fatty acids and cholesterol in the blood serum, are of considerable importance.

It is known per se that the free 3-methylpyrazole-5-carboxylic acid shows corresponding activity.

When feeding 3-methylpyrazole-5-carboxylic acids to starving rats, David L. Smith et al (J. Med. Chem. 8 (3), 350-3 (1965)) found that this compound exceed the hypoglycaemic activity of tolbutamide (N-butyl-N'-toluene-p-sulphonylurea) by two hundred times.

It has been reported from other sources (G. Gerritzen et al, Advan. Exp. Med. Biol. (1969) 4, 93–103 and G. Tamasi et al, Med. Pharmacol. Exp. 16 (1967) 6, 573-8) that, when administered in small doses to starving normal rats, this substance reduces the level of free fatty acids and triglycerides in the serum. However, the tachyphylaxia of this substance, as observed by the authors, limits its suitability for therapeutic application.

Surprisingly, however, the derivatives according to the invention, derived from the base theophylline, have no tachyphylactic properties despite their particularly pronounced lipolysis-inhibiting effect.

The invention is illustrated by the following Examples.

EXAMPLE 1

7-[3-(N-methyl-N-2-hydroxyethyl)-amino-2-hydroxypropyl]-1,3-dimethylxanthine-3-methylpyrazole-5-carboxylate 8.6 g (0.0276 mol) of 7-[3-(N-methyl-N-2-hydroxyethyl)amino-2-hydroxypropyl]-1,3-dimethylxanthine (TLC-pure) are dissolved in 30 ml of absolute ethanol, followed by the dropwise addition with stirring (magnetic stirrer) at boiling temperature of a solution of 3.5 g (0.0276 mol) of 3-methylpyrazole-5-carboxylic acid (TLC-pure) in 100 ml of absolute ethanol.

On completion of the addition, the clear solution is allowed to cool to room temperature. Colourless crystals precipitate after a while, being filtered off under suction.

Another crystal fraction is obtained from the mother liquor concentrated in vacuo by leaving it standing in a refrigerator. This additional crystal fraction is combined with the first and recrystallised from ethanol. The salt thus obtained melts at 161.5 to 162.5°C.

Total yield: 10.2 g = 84% of the theoretical

| Analysis: | C | H | N | O |
|---|---|---|---|---|
| Calc.: | 49.42 | 6.22 | 21.95 | 22.41 |
| Found: | 49.97 | 6.24 | 21.68 | 22.05 |

EXAMPLES 2 to 12

The other compounds of general formula I listed in Table I were produced in accordance with Example 1.

Table I

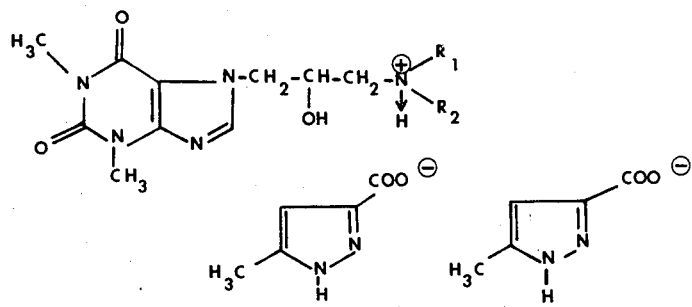

| Exp. No. | $R_1$ | $R_2$ | Melting point in °C solvent for recrystallisation | Yield in % of theoretical | | Combustion analysis | | | |
|---|---|---|---|---|---|---|---|---|---|
| | | | | | | C | H | N | O |
| 1 | —CH₃ | —CH₂—CH₂—OH | 161.5–162.5 ethanol | 84 | Calc.: Found: | 49.42 49.97 | 6.22 6.24 | 21.95 21.68 | 22.41 22.05 |
| 2 | H | (bicyclic) | 195–197 ethyl acetate/ petrol 100–40 | 45 | Calc.: Found: | 55.69 55.95 | 6.80 6.77 | 20.66 19.90 | 16.86 17.22 |
| 3 | H | —CH₂—CH₂—OH | 212.5–214 aqueous ethanol/ ethyl acetate | 91 | Calc.: Found: | 48.22 48.04 | 5.95 5.92 | 23.11 23.06 | 22.64 22.96 |
| 4 | H | —C(CH₃)₂—CH₂—CH₂—OH | 157–159 ethanol | 70 | Calc.: Found: | 51.60 51.65 | 6.72 6.80 | 21.06 20.96 | 20.62 20.70 |
| 5 | H | —CH₂—CH₂—O—C₂H₅ | 139–141 ethanol | 74 | Calc.: Found: | 50.54 50.69 | 6.48 6.38 | 21.72 22.20 | 21.26 20.70 |
| 6 | H | —CH₂—CH₂—CH₂—OC₂H₅ | 193–193.5 ethyl acetate/ ethanol | 57 | Calc.: Found: | 51.61 52.14 | 6.71 6.81 | 21.06 20.85 | 20.62 20.16 |
| 7 | H | —CH₂—CH₂—(phenyl) | 215.216.5 ethyl acetate/ ethanol | 86 | Calc.: Found: | 57.14 57.08 | 6.04 6.18 | 20.28 19.71 | 16.55 16.99 |
| 8 | H | —C(CH₃)₂—CH₂—CH₃ | 151–152 dioxan/ petroleum ether | 68 | Calc.: Found: | 53.44 53.40 | 6.95 6.91 | 21.81 21.52 | 17.80 18.20 |

Table I-continued

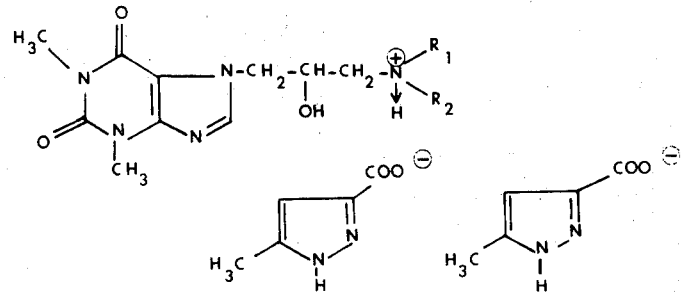

| Exp. No. | $R_1$ | $R_2$ | Melting point in °C solvent for re-crystallisation | Yield in % of theo-retical | | Combustion analysis C | H | N | O |
|---|---|---|---|---|---|---|---|---|---|
| 9 | —CH$_2$—CH$_3$ | —CH$_2$—CH$_3$ | 167.0–168.5 isopropanol | 82 | Calc.: Found: | 52.40 52.51 | 6.71 6.61 | 22.51 22.56 | 18.37 18.49 |
| 10 | —CH$_2$—CH$_2$CH$_3$ | ⬡ | 98–99 ethyl acetate/ethanol | 73 | Calc.: Found: | 57.26 57.09 | 7.41 7.67 | 19.47 18.78 | 15.88 16.56 |
| 11 | —CH$_2$—(CH$_2$)$_2$—CH$_3$ | ⬡ | 95.5–97 ethanol | 43 | Calc.: Found: | 58.02 57.21 | 7.60 7.76 | 18.94 18.96 | 15.45 15.94 |
| 12 | ⬡O | | 224–225 | 58 | Calc.: Found: | 50.77 50.67 | 6.06 6.06 | 21.81 21.64 | 21.35 21.61 |

PHARMACOLOGICAL INVESTIGATIONS

Investigations on a total of 260 Wistarrats were conducted with 7-[3-(N-methyl-N-2-hydroxyethyl)-amino-2-hydroxypropyl]-1,3-dimethylxanthine-3-methyl-pyrazole-5-carboxylate. This compound significantly influences the free fatty acids (FFS) after the application of doses down to 2 mg/kg body weight both in normal animals and in hyperlipacidaemic animals (starved animals, alcohol animals). The lypolysis-inhibiting effect is more pronounced than that of the free 3-methylpyrazole-5-carboxylic acid, which was found in comparative examinations with equimolar dosage and which was reflected in different significance limits especially 6 hours after application.

It was also found that the compound 7-[3-(N-methyl-N-2-hydroxyethyl)-amino-2-hydroxypropyl]-1,3-dimethylxanthine-3-methylpyrazole-5-carboxylate significantly reduces the cholesterol level of starved rats when administered perorally in a dose of 100 mg/kg of body weight.

In doses of down to 10 mg/kg of body weight, it also significantly reduces the serum triglyceride level of normal animals. By contrast, equimolecular doses of the free acid produce only a relatively weak, i.e. insignificant effect.

In hyperlipacidaemic rats treated with octylphenol polyethylene glycolether, the above-mentioned compound according to the invention produces a significant reduction in the triglyceride level.

After the repeated application of 100 mg/kg of body weight over a period of 4 days, the compound showed a uniform and, in some cases, even increased effect on the serum triglycerides and the serum cholesterol.

Even on the fourth day, both parameters were still significantly reduced.

It is known from the works of Gerritzen et al that pretreatment of the test animals for 4 to 5 days with 3-methylpyrazole-5-carboxylic acid weakens the effect on the free fatty acid content of the plasma. We were able to confirm the results of these tests. However, we found that the comound 7-[3-(N-methyl-N-2-hydroxyethyl)-amino-2-hydroxypropyl]-1,3-dimethylxanthine-3-methylpyrazole-5-carboxylate does not have this effect.

The results of our tests are shown in Table 13 and FIG. 4.

The results are shown in Tables 1 to 13 and in FIGS. 1 to 4.

The LD$_{50}$ of the compound in mice amounts to more than 1000 mg/kg per oral and to 540 mg/kg i.v.

The other compounds according to the invention show equally pronounced pharmacological effects.

TABLE 1

Examination of the influence of 7-[3-(N-methyl-N-2-hydroxyethyl)-amino-2-hydroxypropyl]-1,3-dimethylxanthine-3-methylpyrazole-5-carboxylate on the serum fatty acids (FFS) of normal animals Test arrangement:
Female rats, starve for 5 hours
Dose: 100 mg/kg body weight, oral by esophagus probe.
Blood removal: 1 hour after application

| Animal No. | Weight/g | FFS µval/ml | |
|---|---|---|---|
| 1 | 199 | 0.56 | |
| 2 | 179 | 0.54 | |
| 3 | 218 | 0.62 | CONTROL |
| 4 | 142 | 0.63 | (H$_2$O esophagus probe) |
| 5 | 214 | 0.56 | |
| 6 | 197 | 0.51 | |
| 7 | 216 | 0.54 | |
| 8 | 195 | 0.59 | |
| 9 | 213 | 0.65 | |
| 10 | 199 | 0.78 | φ 0.60 µval/ml |
| 1 | 200 | 0.51 | |
| 2 | 186 | 0.58 | |
| 3 | 219 | 0.52 | TEST SERIES |
| 4 | 194 | 0.56 | |
| 5 | 198 | 0.51 | |
| 6 | 204 | 0.57 | |
| 7 | 215 | 0.48 | |
| 8 | 198 | 0.54 | φ 0.53 µval/ml |

Table 2

Examination of the influence of 7-[3-(N-methyl-N-2-hydroxyethyl)-amino-2-hydroxypropyl]-1,3-dimethylxanthine-3-methylpyrazole-5-carboxylate on the serum fatty acids (FFS) of hyperlipacidaemic rats Test arrangement: a) Hunger lipolysis
Male Rats, starve for 17 hours
Dose: 100 mg/kg body weight, oral by esophagus probe.
Blood removal: 1 hour after application

| Animal No. | Weight/g | FFS µval/ml | |
|---|---|---|---|
| 1 | 162 | 0.52 | |
| 2 | 197 | 0.81 | |
| 3 | 181 | 1.10 | |
| 4 | 195 | 1.03 | |
| 5 | 145 | 0.79 | CONTROL |
| 6 | 140 | 0.76 | (H$_2$O-esophagus probe) |
| 7 | 140 | 1.30 | |
| 8 | 147 | 0.65 | |
| 9 | 146 | 1.06 | |
| 10 | 157 | 0.79 | φ 160 g BW/0.91 µval/ml |
| 11 | 165 | 0.95 | |
| 12 | 155 | 0.92 | |
| 13 | 158 | 1.09 | |
| 14 | 159 | 0.99 | |
| 15 | 148 | 0.94 | |
| 1 | 208 | 0.29 | |
| 2 | 178 | 0.34 | |
| 3 | 173 | 0.54 | |
| 4 | 189 | 0.47 | TEST SERIES |
| 5 | 144 | 0.67 | |
| 6 | 140 | 0.46 | |
| 7 | 148 | 0.44 | |
| 8 | 144 | 0.43 | |
| 9 | 146 | 0.39 | |
| 10 | 148 | 0.47 | φ 160 g BW/0.46 µval/ml, p<0.001 |
| 11 | 158 | 0.48 | |
| 12 | 154 | 0.51 | |
| 13 | 162 | 0.47 | |
| 14 | 158 | 0.45 | |
| 15 | 152 | 0.51 | |

Table 3

Examination of the influence of 7-[3-(N-methyl-N-2-hydroxyethyl)-amino-2-hydroxypropyl]-1,3-dimethylxanthine-3-methylpyrazole-5-carboxylate on the serum fatty acids (FFS) of hyperlipacidaemic rats
b) Alcohol lipolysis Test arrangement:
rats, starve for 5 hours.
Dose: alcohol 2g/kg body weight in 20% solution i.v.,
Dose: active principle according to the invention 100 mg/kg body weight, oral by esophagus probe 3 hours before blood removal

| Animal No. | Weight(g) | FFS (µval/ml) | |
|---|---|---|---|
| 1 | 218 | 0.45 | |
| 2 | 206 | 0.77 | |
| 3 | 223 | 0.50 | |
| 4 | 234 | 0.66 | CONTROL |
| 5 | 188 | 0.73 | |
| 6 | 211 | 0.75 | φ 0.64 µval/ml |
| 7 | 167 | 0.62 | |
| 8 | 182 | 0.66 | |
| 9 | 160 | 0.45 | |
| 10 | 189 | 0.81 | |
| 1 | 161 | 0.77 | |
| 2 | 181 | 1.00 | |
| 3 | 177 | 1.06 | |
| 4 | 182 | 0.78 | ALCOHOL SERIES |
| 5 | 178 | 0.85 | |
| 6 | 184 | 0.50 | φ 0.79 µval/ml |
| 7 | 190 | 0.74 | p<0.05 |
| 8 | 169 | 0.78 | |
| 9 | 166 | 0.73 | |
| 10 | 176 | 0.70 | |
| 1 | 150 | 0.45 | |
| 2 | 164 | 0.58 | |
| 3 | 188 | 0.59 | ALCOHOL SERIES + active principle according to the invention |
| 4 | 178 | 0.60 | |
| 5 | 168 | 0.52 | |
| 6 | 188 | 0.56 | |
| 7 | 178 | 0.43 | φ 0.56 µval/ml |
| 8 | 170 | 0.66 | p<0.001 |
| 9 | 141 | 0.67 | |
| 10 | 165 | 0.53 | |

Table 4

Examination of the influence of 7-[3-(N-methyl-N-2-hydroxyethyl)-amino-2-hydroxypropyl]-1,3-dimethylxanthine-3-methylpyrazole-5-carboxylate on the free fatty acids (FFS) in starved animals 1 hour after application Dose - Effect relations

| CONTROL | | 7-[3-(N-methyl-N-2-hydroxyethyl)-amino-2-hydroxypropyl]-1,3-dimethylxanthine-3-methylpyrazole-5-carboxylate | | | |
|---|---|---|---|---|---|
| FFS µval/ml | n | Dose mg/kg | FFS µval/ml | n | |
| 0.91* | 15 | 100 | 0.46* | 15 | *p<0.001 |
| 1.08** | 10 | 50 | 0.40** | 10 | **p<0.001 |
| 1.02 | 2 | 40 | 0.48 | 5 | |
| 1.02 | 2 | 30 | 0.54 | 4 | |
| 0.90 | 3 | 20 | 0.56 | 5 | |
| 0.97 | 5 | 10 | 0.53 | 10 | |
| 0.83 | 3 | 5 | 0.43 | 5 | |
| 0.86 | 7 | 2.5 | 0.50 | 13 | |
| 0.87** | 10 | 2.0 | 0.51*** | 10 | ***p<0.001 |

Table 5

Comparative examinations of the influence of 7-[3-(N-methyl-N-2-hydroxyethyl)-amino-2-hydroxypropyl]-1,3-dimethylxanthine-3-methylpyrazole-5-carboxylate and 3-methylpyrazole-5-carboxylic acid on the free fatty acids (FFS) in starved animals 1 hour after application
(cf. FIG. 1)

| CONTROL | 7-[3-(N-methyl-N-2-hydroxyethyl)-amino-2-hydroxypropyl]-1,3-dimethylxanthine-3-methylpyrazole-5-carboxylate 50 mg/kg | 3-methylpyrazole-5-carboxylic acid 15 mg/kg |
|---|---|---|
| FFS µval/ml | FFS µval/ml | FFS µval/ml |
| 0.96 | 0.39 | 0.41 |

Table 5-continued

Comparative examinations of the influence of 7-[3-(N-methyl-N-2-hydroxyethyl)-amino-2-hydroxypropyl]-1,3-dimethylxanthine-
-3-methylpyrazole-5-carboxylate and 3-methylpyrazole-5-
carboxylic acid on the free fatty acids (FFS) in starved
animals 1 hour after application
(cf. FIG. 1)

| CONTROL FFS $\mu$val/ml | 7-[3-(N-methyl-N-2-hydroxyethyl)-amino-2-hydroxypropyl]-1,3-di-methylxanthine-3-methylpyrazole-5-carboxylate 50 mg/kg FFS $\mu$val/ml | 3-methylpyrazole-5-carboxylic acid 15 mg/kg FFS $\mu$val/ml |
|---|---|---|
| 1.08 | 0.44 | 0.43 |
| 1.33 | 0.46 | 0.59 |
| 1.07 | 0.40 | 0.52 |
| 1.32 | 0.35 | 0.67 |
| 0.98 | 0.45 | 0.37 |
| 1.02 | 0.37 | 0.40 |
| 1.12 | 0.32 | 0.37 |
| 0.88 | 0.39 | 0.54 |
| 0.99 | 0.41 | 0.44 |
| $\bar{x}$ 1.08 | 0.40 | 0.47 |
| n=10 | n=10 | n=10 |
|  | p<0.001 | p<0.001 |

Table 6

Comparative examinations of the influence of 7-[3-(N-methyl-N-2-hydroxyethyl)-amino-2-hydroxypropyl]-1,3-dimethyl-xanthine-3-methylpyrazole-5-carboxylate and 3-methyl-pyrazole-5-carboxylic acid on the free fatty acids (FFS) in starved animals 6 hours after application
(cf. FIG. 1)

| CONTROL FFS $\mu$val/ml | 7-[3-(N-methyl-N-2-hydroxyethyl-amino-2-hydroxypropyl] 1,3-dimethylxanthine-3-methylpyrazole-5-carboxylate 50 mg/kg BW p.o. FFS $\mu$val/ml | 3-methyl-pyrazole-5-carboxylic acid 15 mg/kg p.o. FFS $\mu$val/ml |
|---|---|---|
| 0.89 | 0.39 | 0.51 |
| 1.06 | 0.35 | 0.50 |
| 0.78 | 0.35 | 0.67 |
| 0.91 | 0.43 | 0.64 |
| 0.88 | 0.35 | 0.50 |
| 0.98 | 0.58 | 0.56 |
| 0.86 | 0.54 | 0.53 |
| 0.80 | 0.63 | 0.61 |
| 0.78 | 0.77 | 0.51 |
| 0.72 | 0.52 | 0.85 |
| 0.70 | 0.51 | 0.67 |
| 0.70 | 0.96 | 0.44 |
| 0.88 | 0.59 | 0.54 |
| 0.91 | 0.43 | 0.58 |
| 0.89 | 0.78 | 1.00 |
| 0.69 | 0.53 | 0.54 |
| 0.65 | 0.96 | 0.47 |
| 0.82 | 0.44 | 0.47 |
| 0.81 | 0.64 | 1.46 |
| 1.00 | 0.85 | 0.56 |
| 1.00 | 0.32 | 1.10 |
| 0.87 |  |  |
| 0.70 |  |  |
| 0.87 |  |  |
| 1.29 |  |  |
| $\bar{x}$ 0.86 | 0.57 | 0.69 |
| n=25 | 21 | 21 |
|  | p<0.001 | p<0.01 |

Table 7

Comparative examinations of the influence of 7-[3-(N-methyl-N-2-hydroxyethyl)-amino-2-hydroxypropyl]-1,3-dimethylxanthine-3-methylpyrazole-5-carboxylate and 3-methylpyrazole-5-carboxylic acid on the serum triglycerides (TG) in normal animals
cf. FIG. 2

Test arrangement:
Rats, starve for 5 hours
Dose: 40 mg/kg body weight of active principle according to the invention, oral by esophagus probe 1 hour before removal of blood
Dose: 12 mg/kg body weight of 3-methylpyrazole-5-carboxylic acid, equim. dosage, 1 hour before removal of blood

| Animal No. | Weight (g) | TG mg % | CONTROL |
|---|---|---|---|
| 1 | 154 | 73.0 |  |
| 2 | 160 | 67.3 |  |
| 3 | 150 | 71.6 | $\bar{x}$ = 66.4 mg % |
| 4 | 164 | 48.7 |  |
| 5 | 171 | 71.6 |  |
| 1 | 188 | 71.6 |  |
| 2 | 178 | 22.9 | 7-[3-(N-methyl-N-2-hydroxy-ethyl)-amino-2-hydroxy-propyl]-1,3-dimethylxanthine-3-methylpyrazole-5-carboxylate |
| 3 | 188 | 15.8 |  |
| 4 | 198 | 15.8 |  |
| 5 | 189 | 18.6 |  |
| 6 | 180 | 41.5 |  |
| 7 | 171 | 40.1 | $\bar{x}$ = 36.3 mg % |
| 8 | 171 | 58.7 | p<0.0027>Ko |
| 9 | 177 | 32.9 |  |
| 10 | 161 | 45.8 |  |
| 1 | 193 | 90.2 |  |
| 2 | 204 | 87.3 | 3-methylpyrazole-5-carboxylic acid |
| 3 | 185 | 90.2 |  |
| 4 | 200 | 58.7 |  |
| 5 | 176 | 107.4 | $\bar{x}$ = 74.1 mg % |
| 6 | 175 | 51.6 |  |
| 7 | 161 | 55.8 |  |
| 8 | 161 | 71.6 |  |
| 9 | 166 | 60.1 |  |
| 10 | 176 | 68.7 |  |

Table 8

Comparative examinations of the influence of 7-[3-(N-methyl-N-2-hydroxyethyl)-amino-2-hydroxypropyl]-1,3-dimethylxanthine-3-methylpyrazole-5-carboxylate and 3-methylpyrazole-5-carboxylic acid on the serum triglycerides (TG) in normal animals (cf. FIG. 2)

Test Arrangement:
Rats, starve for 5 hours
Dose: 10 mg/kg body weight of active principle according to the invention, oral by esophagus probe 1 hour before blood removal
Dose: 3 mg/kg body weight of 3-methylpyrazole-5-carboxylic acid, equim. dosage, oral by esophagus probe 1 hour before blood removal

| Animal No. | Weight (g) | TG mg % | CONTROL |
|---|---|---|---|
| 1 | 217 | 105.9 | |
| 2 | 227 | 63.0 | |
| 3 | 220 | 110.3 | |
| 4 | 190 | 60.1 | |
| 5 | 200 | 127.4 | |
| 6 | 200 | 113.1 | $\bar{x}$ = 86.3 mg % |
| 7 | 211 | 61.6 | |
| 8 | 196 | 63.0 | |
| 9 | 200 | 98.8 | |
| 10 | 207 | 60.1 | |
| 1 | 188 | 48.7 | |
| 2 | 162 | 54.4 | 7-[3-(N-methyl-N-2-hydroxyethyl)- |
| 3 | 189 | 83.1 | amino-2-hydroxypropyl]-1,3-di- |
| 4 | 189 | 54.4 | methylxanthine-3-methylpyrazole- |
| 5 | 181 | 55.8 | 5-carboxylate |
| 6 | 198 | 74.4 | |
| 7 | 209 | 81.6 | $\bar{x}$ = 59.8 mg % |
| 8 | 198 | 51.5 | p<0.05>Ko |
| 9 | 183 | 54.4 | |
| 10 | 183 | 40.1 | |
| 1 | 188 | 137.4 | |
| 2 | 180 | 87.3 | |
| 3 | 168 | 70.2 | 3-methylpyrazole-5- |
| 4 | 181 | 74.4 | carboxylic acid |
| 5 | 185 | 50.1 | |
| 6 | 207 | 43.0 | $\bar{x}$ = 67.7 mg % |
| 7 | 212 | 57.2 | p>0.05 → Ko. |
| 8 | 190 | 51.5 | p>0.05 → xant.-carbox. |
| 9 | 190 | 32.9 | |
| 10 | 214 | 73.0 | |

Table 9

Triglycerides

Test arrangement:

Male rats, starve for 22 hours, ether narcosis, heart puncture
Dose: 1000 mg/kg of octylphenyl polyethylene glycolether i.v. 6 hours before blood removal Dose: 100 mg/kg of 7-[3-(N-methyl-N-2-hydroxyethyl)-amino-2-hydroxypropyl]-1,3-dimethylxanthine-3-methylpyrazole-5-carboxylate by esophagus probe, 6 hours, 4 hours and 2 hours before blood removal

| Animal No. | Weight (g) | TG mg % | CONTROL |
|---|---|---|---|
| 1 | 199 | 746.1 | |
| 2 | 200 | 786.2 | Octylphenol polyethylene |
| 3 | 178 | 776.1 | glycolether |
| 4 | 194 | 764.7 | 1000 mg/kg i.v. |
| 5 | 186 | 791.9 | 6 hours before killing |
| 6 | 197 | 764.7 | |
| 7 | 216 | 777.6 | |
| 8 | 160 | 784.7 | |
| 9 | 208 | 794.8 | |
| 10 | 176 | 784.7 | |
| | | $\bar{x}$ = 777.2 | |
| 1 | 196 | 644.4 | Octylphenol polyethyelene |

Table 9-continued

Triglycerides

Test arrangement:

Male rats, starve for 22 hours, ether narcosis, heart puncture
Dose: 1000 mg/kg of octylphenyl polyethylene glycolether i.v. 6 hours before blood removal Dose: 100 mg/kg of 7-[3-(N-methyl-N-2-hydroxyethyl)-amino-2-hydroxypropyl]-1,3-dimethylxanthine-3-methylpyrazole-5-carboxylate by esophagus probe, 6 hours, 4 hours and 2 hours before blood removal

| Animal No. | Weight (g) | TG mg % | CONTROL |
|---|---|---|---|
| 2 | 188 | 687.4 | glycolether |
| 3 | 186 | 701.6 | 1000 mg/kg i.v. |
| 4 | 198 | 707.4 | 6 hours before killing |
| 5 | 209 | 701.6 | + |
| 6 | 196 | 610.0 | 100 mg/kg of 7-[3-(N-methyl- |
| 7 | 198 | 703.1 | N-2-hydroxyethyl)-amino-2- |
| 8 | 214 | 695.9 | hydroxypropyl]-1,3-dimethyl- |
| 9 | 197 | 711.7 | xanthine-3-methylpyrazole- |
| 10 | 197 | 707.4 | 5-carboxylate per os |
| | | $\bar{x}$ 687.0 | 6, 4 and 2 hours before killing |
| | | | p<0.001 |

Table 10

Assaying for cholesterol

Male Rats, starve for 18 hours, ether narcosis, heart puncture

7-[3-(N-methyl-N-2-hydroxyethyl)-amino-2-hydroxypropyl]-1,3-dimethylxanthine-3-methylpyrazole-5-carboxylate

| | Control Animals | | 1 hour before killing 100 mg/kg of 7-[3-(N-methyl-N-2-hydroxyethyl)-amino-2-hydroxypropyl]-1,3-dimethylxanthine-3-methylpyrazole-5-carboxylate per os | |
|---|---|---|---|---|
| No. | Weight (g) | Cholesterol mg % | No. | Weight (g) | Cholesterol mg % |
| 1 | 204 | 90.52 | 1 | 219 | 78.45 |
| 2 | 240 | 76.72 | 2 | 152 | 50.86 |
| 3 | 238 | 82.76 | 3 | 198 | 57.76 |
| 4 | 250 | 79.31 | 4 | 196 | 47.71 |
| 5 | 230 | 65.52 | 5 | 203 | 62.07 |
| 6 | 225 | 74.14 | 6 | 178 | 48.28 |
| 7 | 150 | 62.07 | 7 | 190 | 65.52 |
| 8 | 210 | 67.24 | 8 | 200 | 56.03 |
| 9 | 200 | 78.45 | 9 | 200 | 65.52 |
| 10 | 236 | 80.17 | 10 | 224 | 38.79 |
| $\bar{x}_{10}$ | 218 | 75.69 $p<0.001$ | $\bar{x}_{10}$ | 196 | 57.07 |

Table 11

Influence on the serum cholesterol of repeated application of 7-[3-(N-methyl-N-2-hydroxyethyl)-amino-2-hydroxypropyl]-1,3-dimethylxanthine-3-methylpyrazole-5-carboxylate 100 mg/kg x/day p.o. rats male, starve for 5 hours, ether narcosis, heart puncture, last application 1 hour before killing (cf. FIG. 3)

| Animal No. | Control | | 1st day | | 2nd day | | 3rd day | | 4th day | |
|---|---|---|---|---|---|---|---|---|---|---|
| | weight | mg % | weight | mg % | weight | mg % | weight | mg % | weight | mg % |
| 1 | 180 g | 64.10 | 177 g | 71.70 | 270 g | 37.4 | 200 g | 52.36 | 200 g | 42.98 |
| 2 | 206 g | 69.23 | 275 g | 49.06 | 210 g | 54.2 | 190 g | 71.24 | 190 g | 37.19 |
| 3 | 208 g | 65.82 | 177 g | 51.89 | 200 g | 55.2 | 200 g | 67.81 | 170 g | 52.07 |
| 4 | 220 g | 78.63 | 198 g | 67.92 | 210 g | 69.9 | 190 g | 50.64 | 170 g | 64.46 |
| 5 | 210 g | 70.09 | 170 g | 51.89 | 200 g | 65.0 | 180 g | 57.51 | 180 g | 80.99 |
| 6 | 240 g | 61.54 | 190 g | 68.87 | 190 g | 69.1 | 190 g | 64.38 | 170 g | 47.11 |
| 7 | 210 g | 60.68 | 178 g | 52.83 | 270 g | 39.4 | 190 g | 62.66 | 180 g | 65.29 |
| 8 | 205 g | 76.92 | 170 g | 52.83 | 260 g | 47.3 | 200 g | 71.24 | 220 g | 58.68 |
| 9 | 210 g | 81.20 | 175 g | 68.87 | 200 g | 49.3 | 180 g | 68.67 | 170 g | 50.41 |
| 10 | 204 g | 84.62 | 150 g | 50.94 | 150 g | 51.2 | 190 g | 60.94 | 170 g | 43.80 |
| $x_{10}$ | 209 g | 71.28 | 176 g | 58.68 | 215 g | 53.8 | 191 g | 62.75 | 182 g | 54.30 |

Table 12

Influence on the serum triglycerides of repeated application of 7-[3-(N-methyl-N-2-hydroxyethyl)-amino-2-hydroxypropyl]-1,3-dimethylxanthine-3-methylpyrazole-5-carboxylate 100 mg/kg x/day p.o. rats male, starve for 5 hours, ether narcosis, heart puncture, last application 1 hour before killing (cf. FIG. 3)

| Animal No. | Control | | 1st day | | 2nd day | | 3rd day | | 4th day | |
|---|---|---|---|---|---|---|---|---|---|---|
| | weight | mg% | weight | mg% | weight | mg% | weight | mg% | weight | mg% |
| 1 | 180 g | 103.1 | 177 g | 85.9 | 270 g | 38.7 | 200 g | 60.1 | 200 g | 30.1 |
| 2 | 206 g | 141.8 | 175 g | 57.3 | 210 g | 61.6 | 190 g | 63.0 | 190 g | 73.0 |
| 3 | 208 g | 153.2 | 177 g | 118.6 | 200 g | 54.4 | 200 g | 90.2 | 170 g | 67.0 |
| 4 | 220 g | 154.6 | 198 g | 104.5 | 210 g | 63.0 | 190 g | 108.8 | 170 g | 64.4 |
| 5 | 210 g | 126.0 | 170 g | 65.9 | 200 g | 95.9 | 180 g | 50.1 | 180 g | 60.1 |
| 6 | 240 g | 136.0 | 190 g | 57.3 | 190 g | 87.3 | 190 g | 97.4 | 170 g | 44.4 |
| 7 | 210 g | 127.4 | 178 g | 104.5 | 270 g | 127.4 | 190 g | 60.1 | 180 g | 44.4 |
| 8 | 205 g | 115.9 | 170 g | 85.9 | 250 g | 74.4 | 200 g | 80.2 | 220 g | 58.7 |
| 9 | 210 g | 144.6 | 175 g | 57.3 | 200 g | 57.2 | 180 g | 105.9 | 170 g | 101.7 |
| 10 | 204 g | 133.2 | 150 g | 88.8 | 150 g | 88.7 | 190 g | 58.7 | 170 g | 67.3 |
| $x_{10}$ | 209 g | 133.6 | 176 g | 82.6 | 215 g | 74.8 | 191 g | 77.4 | 182 g | 61.1 |

Table 13

Influence of 7-[3-(N-methyl-N-2-hydroxyethyl)-amino-2-hydroxypropyl]-1,3-dimethylxanthine-3-methylpyrazole-5-carboxylate on the free fatty acids (FFS)

Rats male, repeated application once daily for 4 days, on the 4th day groups of 10 animals were killed at intervals of 30 minutes, 1 hour and 2 hours after the last application by ether narcosis and heart puncture. 10 controls were given esophagus probe, animals starved for 17 hours before killing (cf. FIG. 4)

Preparation: 7-[3-(N-methyl-2-hydroxyethyl)-amino-2-hydroxypropyl]-1,3-dimethylxanthine-3-methylpyrazole-5-carboxylate 50 mg/kg peroral 3-methylpyrazole-5-carboxylic acid (3-MPC) eq./kg $\triangleq$ 15 mg/kg peroral Method: Acta. Biol. Vol. 12, 520 (1964)

| Animal No. | Weight (g) | µval/ml plasma | CONTROL |
|---|---|---|---|
| 1 | 160 | 1.17 | |
| 2 | 210 | 1.21 | |
| 3 | 230 | 1.24 | |
| 4 | 200 | 1.28 | |
| 5 | 230 | 1.12 | |
| 6 | 260 | 1.41 | |
| 7 | 230 | 1.30 | |
| 8 | 240 | 1.24 | |
| 9 | 240 | 1.49 | |
| 10 | 220 | 1.31 | |
| $\bar{x}_{10}$ | 222 | 1.27 | |
| 1 | 270 | 0.72 | 7-[3-(N-methyl-N-2- |
| 2 | 240 | 0.94 | hydroxyethyl)-amino-2- |
| 3 | 240 | 0.69 | hydroxypropyl]-1,3- |
| 4 | 240 | 0.83 | dimethylxanthine-3- |
| 5 | 230 | 1.36 | methylpyrazole-5- |
| 6 | 230 | 0.89 | carboxylate |
| 7 | 230 | 0.66 | 4 × appl. 50 mg/kg p.o. |
| 8 | 240 | 0.67 | 30' after last application + |
| 9 | 240 | 0.86 | |
| 10 | 240 | 1.07 | |
| $\bar{x}_{10}$ | 240 | 0.87 | $p<0.001$ |
| 1 | 230 | 0.75 | 7-[3-(N-methyl-N-2- |
| 2 | 200 | 0.42 | hydroxyethyl)-amino-2- |
| 3 | 220 | 0.45 | hydroxypropyl]-1,3- |
| 4 | 220 | 0.56 | dimethylxanthine-3- |
| 5 | 240 | 0.67 | methylpyrazole-5- |
| 6 | 230 | 0.54 | carboxylate |
| 7 | 200 | 0.86 | 4 × appl. 50 mg/kg p.o. |
| 8 | 230 | 0.63 | 1 h after last appl. + |
| 9 | 260 | 0.98 | |
| 10 | 230 | 0.89 | |
| $\bar{x}_{10}$ | 226 | 0.68 | $p<0.001$ |
| 1 | 250 | 0.79 | 7-[3-(N-methyl-N-2- |
| 2 | 240 | 0.58 | hydroxyethyl)-amino-2- |
| 3 | 220 | 0.94 | hydroxypropyl]-1,3- |
| 4 | 190 | 0.80 | dimethylxanthine-3- |
| 5 | 190 | 1.10 | methylpyrazole-5- |
| 6 | 240 | 1.07 | carboxylate |
| 7 | 210 | 0.84 | 4 × appl. 50 mg/kg p.o. |
| 8 | 270 | 0.90 | 2 h after last appl.+ |
| 9 | 260 | 0.97 | |
| 10 | 280 | 0.83 | |
| $\bar{x}_{10}$ | 235 | 0.88 | $p<0.001$ |
| 1 | 210 | 0.66 | 3-methylpyrazole-5- |
| 2 | 190 | 0.59 | carboxylic acid |
| 3 | 220 | 0.53 | |
| 4 | 250 | 0.91 | 15 mg/kg p.o. |
| 5 | 210 | 0.56 | 4 × appl. |
| 6 | 210 | 0.95 | 30' after last |
| 7 | 250 | 1.02 | application + |
| 8 | 220 | 0.81 | |
| 9 | 240 | 0.80 | |
| 10 | 210 | 0.60 | |
| $\bar{x}_{10}$ | 221 | 0.74 | $p<0.001$ |
| 1 | 230 | 0.75 | 3-methylpyrazole-5- |
| 2 | 220 | 0.73 | carboxylic acid |
| 3 | 210 | 0.95 | |
| 4 | 200 | 0.96 | 15 mg/kg p.o. |
| 5 | 200 | 1.03 | 4 × appl. |
| 6 | 230 | 1.16 | 1 h after last |
| 7 | 190 | 1.08 | application |
| 8 | 210 | 0.84 | |

Table 13-continued

Influence of 7-[3-(N-methyl-N-2-hydroxyethyl)-amino-2-hydroxypropyl]-1,3-dimethylxanthine-3-methylpyrazole-5-carboxylate on the free fatty acids (FFS)

Rats male, repeated application once daily for 4 days, on the 4th day groups of 10 animals were killed at intervals of 30 minutes, 1 hour and 2 hours after the last application by ether narcosis and heart puncture. 10 controls were given esophagus probe, animals starved for 17 hours before killing (cf. FIG. 4)

Preparation: 7-[3-(N-methyl-2-hydroxyethyl)-amino-2-hydroxypropyl]-1,3-dimethylxanthine-3-methylpyrazole-5-carboxylate 50 mg/kg peroral 3-methylpyrazole-5-carboxylic acid (3-MPC) eq./kg≙15 mg/kg peroral Method: Acta. Biol. Vol. 12, 520 (1964)

| Animal No. | Weight (g) | μval/ml plasma | CONTROL |
|---|---|---|---|
| 9 | 220 | 1.24 | |
| 10 | 240 | 0.92 | |
| $\bar{x}_{10}$ | 215 | 0.97 | p<0.001 |
| 1 | 200 | 0.62 | 3-methylpyrazole-5- |
| 2 | 220 | 0.59 | carboxylic acid |
| 3 | 230 | 0.51 | |
| 4 | 250 | 0.70 | 15 mg/kg p.o. |
| 5 | 250 | 0.88 | 4 × appl. |
| 6 | 270 | 0.84 | 2 h after last |
| 7 | 220 | 1.27 | application |
| 8 | 230 | 1.20 | |
| 9 | 250 | 0.86 | |
| $\bar{x}_9$ | 235 | 0.83 | p<0.001 |

We claim:
1. A 3-Methylpyrazole-5-carboxylate corresponding to the general formula

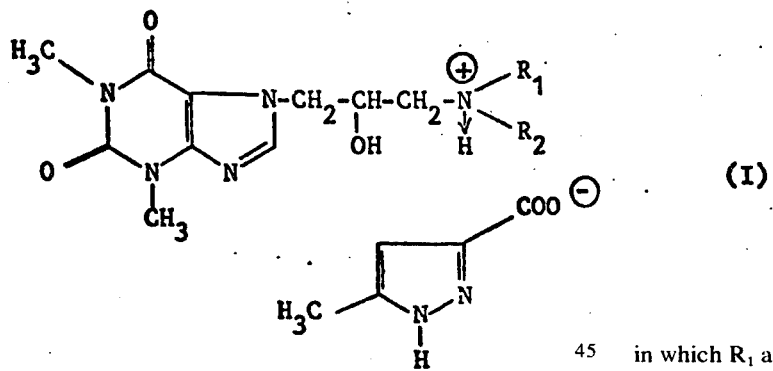

(I)

in which $R_1$ and $R_2$ when taken separately represents hydrogen, a straight-chain or branched alkyl radical with 1 to 5 carbon atoms, a hydroxyalkyl radical with 1 to 5 carbon atoms, an alkoxyalkyl radical of 1 to 5 carbon atoms in each of the alkoxy and alkyl groups thereof, a phenylethyl group or norbornyl group or, $R_1$ and $R_2$, when taken together with the nitrogen atom to which they are attached, represent a morpholine radical.

2. The compound according to claim 1 wherein $R_1$ is methyl and $R_2$ is hydroxyethyl.

3. A composition for treating a hyperlipacidaemic animal containing a compound of claim 1 in a hyperlipacidaemic effective amount in combination with a pharmacologically compatible carrier.

* * * * *

UNITED STATES PATENT AND TRADEMARK OFFICE
CERTIFICATE OF CORRECTION

PATENT NO. : 3,980,646
DATED : September 14, 1976
INVENTOR(S) : Günter Brenner, et al It is certified that error appears in the above-identified patent and that said Letters Patent are hereby corrected as shown below:

Column 10, line 11 - Table 6, 3rd Column:

change "15 mk/kg p.o." to --15 mk/kg BW p.o.--.

Column 10, line 31 - Table 6, 1st Column:

change "x 0.86" to --$\bar{x}$ 0.86--.

Columns 13 and 14 - Table 11, 1st Column: (bottom)

change "$x_{10}$" to --$\bar{x}_{10}$--

Columns 13 and 14 - Table 12, 1st Column: (bottom)

change "$x_{10}$" to --$\bar{x}_{10}$--

Signed and Sealed this

Twenty-eighth Day of December 1976

[SEAL]

Attest:

RUTH C. MASON
*Attesting Officer*

C. MARSHALL DANN
*Commissioner of Patents and Trademarks*